(12) United States Patent
Gutman et al.

(10) Patent No.: US 6,492,522 B1
(45) Date of Patent: Dec. 10, 2002

(54) PROCESS AND INTERMEDIATES FOR PRODUCTION OF DONEPEZIL AND RELATED COMPOUNDS

(75) Inventors: Arie L. Gutman, Haifa (IL); Eleonora Shkolnik, Nesher (IL); Boris Tishin, Haifa (IL); Genady Nisnevich, Nesher (IL); Igor Zaltzman, Haifa (IL)

(73) Assignee: Finetech Laboratories Ltd., Haifa (IL)

( * ) Notice: Subject to any disclaimer, the term of this patent is extended or adjusted under 35 U.S.C. 154(b) by 0 days.

(21) Appl. No.: 09/763,245

(22) PCT Filed: Aug. 11, 1999

(86) PCT No.: PCT/IL99/00436

§ 371 (c)(1),
(2), (4) Date: May 24, 2001

(87) PCT Pub. No.: WO00/09483

PCT Pub. Date: Feb. 24, 2000

(30) Foreign Application Priority Data

Aug. 17, 1998 (IL) .................................................. 125809

(51) Int. Cl.$^7$ ...................... C07D 211/32; C07D 211/34
(52) U.S. Cl. ...................... 546/206; 546/205; 546/238; 546/342; 558/179
(58) Field of Search ................................ 546/205, 206, 546/238, 342; 558/179

(56) References Cited

U.S. PATENT DOCUMENTS

| 3,476,759 A | 11/1969 | Paragamian |
| 5,100,901 A | 3/1992 | Sugimoto et al. |

FOREIGN PATENT DOCUMENTS

| EP | 0 742 207 A1 | 11/1996 |
| WO | 97/22584 A1 | 6/1997 |

OTHER PUBLICATIONS

Hachiro Sugimoto et al., "Synthesis and Structure–Activity Relationships of Acetylcholinesterase Inhibitors: 1–Benzyl–4–[(5,6–deimethoxy–1–oxoindan–2–yl)methyl]piperidine Hydrochloride and Related Compounds", J. Med. Chem. vol. 38, pp. 4821–4829, 1995.

Derwent AbstractXP–002120528, of "JP 03 279343 A" published Dec. 10, 1991 assigned to Mitsubishi Kasei Corp. 4, Derwent Publications Ltd.

Hideto Miyoshi et al., "Specificity of Pyridinum Inhibitors of the Ubiquinone Reduction Sites In Mitochondrial Complex I", Journal of Biological Chemistry, vol. 273, n. 28, pp. 17368–17374, 1998.

Saul Patai: "The Chemistry of the Carbonyl Group", Interscience Publishers, pp. 252–255 and 298–299, 1966.

*Primary Examiner*—Ceila Chang
(74) *Attorney, Agent, or Firm*—Browdy and Neimark, P.L.L.C.

(57) ABSTRACT

The present invention relates to a new process for the preparation of acetylcholinesterase inhibitors of formula (I) or a salt thereof, wherein: $R^1$ is N-acyl-4-piperidyl; N-alkoxycarbonyl-4-piperidyl; N-alkyl-4-piperidyl; N-benzyl-4-piperidyl; N-(ω-aralkyl)-4-piperidyl; 4-pyridyl; $R^4$, $R^5$, $R^6$, and $R^7$ are identical or different and each represents hydrogen, straight-chain or branched alkyl, aryl, hydroxy, alkoxy, aryloxy, benzyloxy, acyloxy, alkylthio, arylthio, benzylthio, acylamino, phthalimido or halogen; n is 1, 2 or 3; m is 1, 2, 3, 4, or 5. This process comprises cyclisation of a compound of formula (II) or salts thereof, wherein $R^1$, $R^4$, $R^5$, $R^6$ and $R^7$, m and n are as defined above; $R^2$ is selected from a derivatised or non-derivatised carboxyl, cyano, N-substituted aminocarbonyl groups or hydrogen; $R^3$ is selected from a derivatised or non-derivatised carboxyl, cyano or N-substituted aminocarbonyl groups, optionally in the presence of acids and/or solvents. One of the most potent acetylcholinesterase inhibitors of the class of compounds prepared according to the present invention is donepezil.

5 Claims, No Drawings

PROCESS AND INTERMEDIATES FOR PRODUCTION OF DONEPEZIL AND RELATED COMPOUNDS

REFERENCE TO RELATED APPLICATIONS

The present application is the national stage under 35 U.S.C. 371 of international application PCT/IL99/00436, filed Aug. 11, 1999 which designated the United States, which international application was published under PCT Article 21 (2) in English.

FIELD OF THE INVENTION

The present invention relates to a new process for the preparation of acetylcholinesterase inhibitors (anti-AchE) such as Donepezil, to some novel intermediates used in this process and to their preparation.

BACKGROUND OF THE INVENTION

Dementia is a chronic progressive organic mental disorder in which there is disturbance of multiple higher cortical functions including memory, thinking, orientation, comprehension, calculation, learning capacity, language and judgement. Alzheimer's Disease is the commonest cause of dementia and is characterized by degeneration of specific nerve cells, presence of neurotic plaques, and neurofibrillary tangles. Definitive diagnosis of Alzheimer's Disease requires demonstration of these characteristic pathological features in brain tissue, although in the vast majority of cases diagnosis is made on clinical grounds alone, where it is more correctly called Senile Dementia of the Alzheimer Type (SDAT).

Various attempts have been made to treat the senile dementia with a drug. It was found that compounds of formula [X] (Scheme 1) possess a high acetylcholinesterase inhibitory activity (Sugimoto, H., et al., *J. Med. Chem.*, v. 38, 481 (1995). One of the most potent acetylcholinesterase inhibitors (anti-AChE) of this class is Donepezil (E2020) [VII].

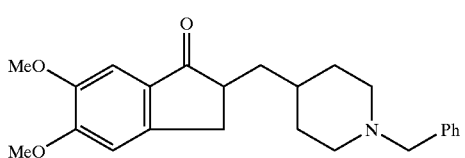

[VII]

Donepezil is a new drug treatment for use in mild to moderate dementia due to SDAT. Donepezil acts by inhibiting acetylcholine esterase, the enzyme responsible for metabolising acetylcholine, thereby enhancing neurotransmitter levels.

The general synthetic route to compounds [X] comprises the condensation of cyclic aromatic ketones [XI] with 1-substituted-4-(ω-formylalkyl)piperidines [XII] followed by reduction of the obtained compounds [XIII] (Scheme 1) (Sugimoto, H., et al., *J. Med. Chem.*, v. 38, 481 (1995); Eisai Co., U.S. Pat. No. 5,100,901).

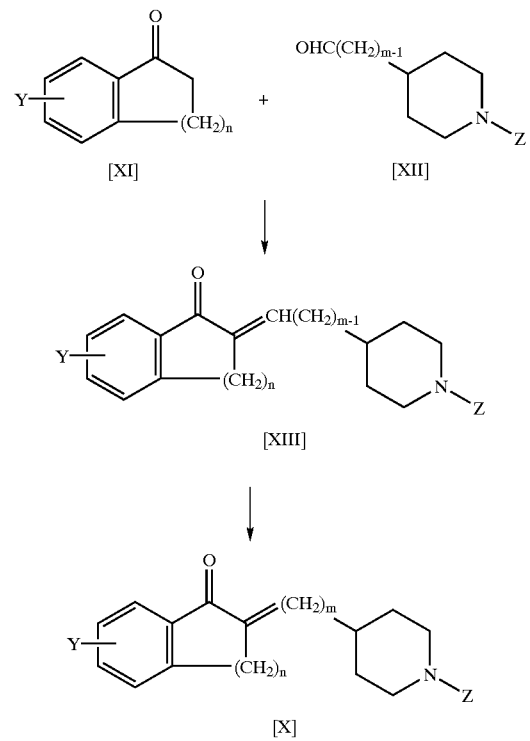

Scheme 1

SUMMARY OF INVENTION

The present invention relates to a process for preparing a compound of formula [I] or a salt thereof:

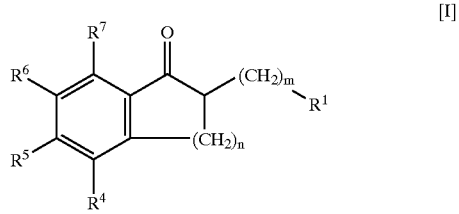

[I]

wherein:

$R^1$ is N-acyl-4-piperidyl; N-alkoxycarbonyl-4-piperidyl; 4-piperidyl; N-alkyl-4-piperidyl; N-benzyl-4-piperidyl; N-(ω-aralkyl)-4-piperidyl; 4-pyridyl;

$R^4$, $R^5$, $R^6$ and $R^7$ are identical or different and each represents hydrogen, straight-chain or branched alkyl, aryl, hydroxy, alkoxy, aryloxy, benzyloxy, acyloxy, alkylthio, arylthio, benzylthio, acylamino, phthalimido or halogen;

n is 1, 2 or 3;

m is 1, 2, 3, 4 or 5;

which process comprises cyclisation of a compound of formula [II] or salts thereof

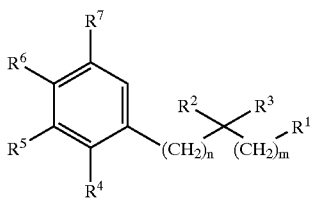

[II]

wherein
$R^1$, $R^4$, $R^5$, $R^6$ and $R^7$, m and n are as defined above;
$R^2$ is selected from a derivatised or non-derivatised carboxyl, cyano, N-substituted aminocarbonyl groups or hydrogen;
$R^3$ is selected from a derivatised or non-derivatised carboxyl, cyano or N-substituted aminocarbonyl groups, optionally in the presence of acids and/or solvents.

According to the present invention, enantiomerically enriched compounds of formula [I] or salts thereof are prepared by cyclisation of optically pure compounds of formula [II], wherein $R^2$ and $R^3$ are different.

The present invention also relates to new compounds of formula [II]:

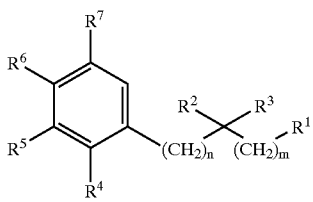

[II]

wherein
$R^1$, $R^2$, $R^3$, $R^4$, $R^5$, $R^6$ and $R^7$, m and n are as defined above, including salts thereof and the optically active enantiomers thereof, with the proviso that when $R^1$ is 4-pyridyl, and n=m=1, then at least one of $R^4$, $R^5$, $R^6$ and $R^7$ does not represent hydrogen or lower alkyl.

The present invention further relates to a process for preparing a compound [II] by the hydrogenation of a compound of formula [VIII] or [IX] or mixtures thereof

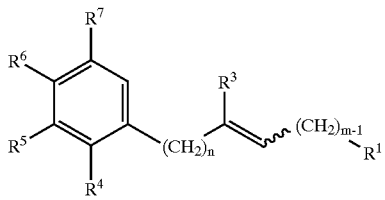

[VIII]

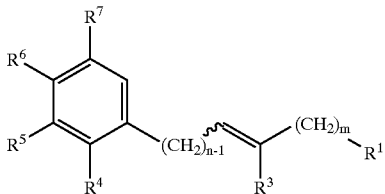

[IX]

wherein
$R^1$, $R^3$, $R^4$, $R^5$, $R^6$, $R^7$, n and m are as defined above.

Alternatively, a compound of the formula [II] can be prepared by reaction of a compound of formula [V]

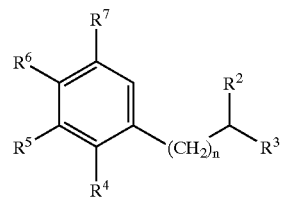

[V]

with a compound of the formula [VI]

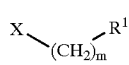

[VI]

in the presence of a strong base,
wherein in all the above formulae, $R^1$, $R^2$, $R^3$, $R^4$, $R^5$, $R^6$, $R^7$, X, m and n are as defined above.

Alternatively, a compound of the formula [II] can be prepared by reacting of compound of formula [III]

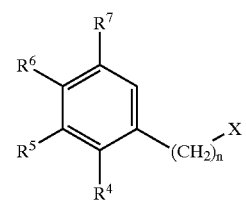

[III]

wherein
X is a facile leaving group,
with a compound of the formula [IV]

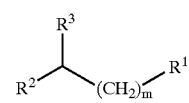

[IV]

in the presence of a strong base as it was shown in one example by Miyoshi, Hideto et. al. (*J. Biol. Chem.*, (1998), 273 (28).

DETAILED DESCRIPTION OF THE INVENTION

The compounds of formula [I] and formula [II] can be prepared as described in the following reaction schemes and discussion. Unless otherwise indicated, the meanings $R^1$, $R^2$, $R^3$, $R^4$, $R^5$, $R^6$, $R^7$, X, n and m in compounds of the formulae [I], [Ia], [II], [IIa], [III], [IIIa], [IV], [IVa], [V], [V], [VI], [VII], [IX], [XX], [XX], [VIIa], [IXa], [XVIIIa], [XIXa] which are shown or mentioned in the reaction schemes and discussion tat follow, are as defined above.

Scheme 2 below refers to a process for the preparation of a compound of formula [I] or salts thereof by cyclisation of a compound of formula [II] or salts thereof:

Scheme 2

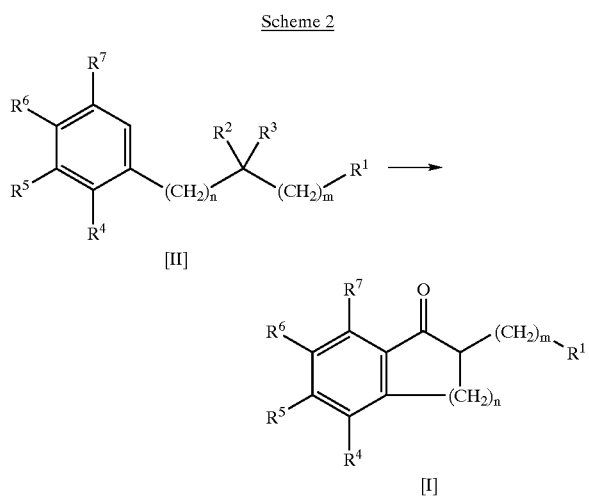

When the above process is carried out with an optically pure compound of formula [II], ($R^2$ and $R^3$ are different), the obtained product is an enantiomically enriched compound of formula [I] or salts thereof.

According to the present invention ester, amido, cyano or ether protecting groups can be hydrolyzed under the conditions of the cyclisation reaction either in the starting compound [II] or in the desired compound [I].

Preferably, the cyclisation is carried out with a previously hydrolysed compound [II], wherein $R^2$ is hydrogen or a carboxyl group and to $R^3$ is a carboxyl group. Compound [II] wherein $R^2$ and $R^3$ are carboxyl groups, are decarboxylated in the course of the intramolecular acylatin.

More preferably, said cyclisation of compound [II] ($R^2$=H, $R^3$=COOH) is carried out under Friedel-Crafts reaction conditions, optionally with previous derivatisation of the $R^3$ carboxylic group to a halocarbonyl group.

Preferably, the cyclisation of the present invention is carried out in the presence of protic acids or Lewis acids or a mixture thereof. Examples of such acids are trifluoromethanesulfonic acid, methanesulfonic acid, polyphosphoric acid, fluoro- or chlorosulfonic acid, sulfuric acid, hydrogen fluoride, hydrogen chloride, zinc chloride, zinc bromide, aluminium chloride, aluminium bromide, titanium chloride, boron fluoride, phosphorus pentoxide, phosphorus oxychloride, phosphorus pentachloride, phosphorus trichloride, thyonyl chloride and sulfuryl chloride.

The cyclisaton of the present invention can be carried out in the presence of a solvent. Preferably, the solvent is selected from dichloromethane, chloroform, dichloroethane, tetrachloroethane, chlorobenzene, dichlorobenzene, nitromethane, nitroethane, nitrobenzene, ether or mixtures thereof.

Pharmaceutically important compounds of formula [Ia] are obtained according to Scheme 3:

Scheme 3

Acids of formula [XV] or [XVI], which are obtained by hydrolysis of the corresponding esters [XIV] and [XVII], undergo cyclisation to yield Donepezil [VII] in high yield and purity (Scheme 4).

Scheme 4

According to another aspect, the present invention relates to new compounds of formula [II] including the optically active enantiomers thereof ($R^2 \neq R^3$) which are used in the cyclisation shown in Scheme 2 above.

Schemes 5 and 6 below refer to processes for preparation of the new compounds of formula [II].

Scheme 5

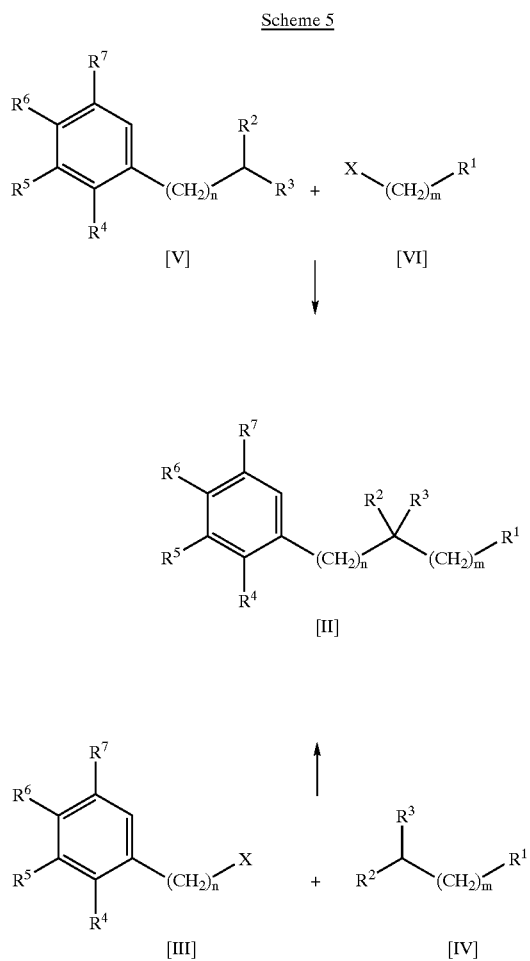

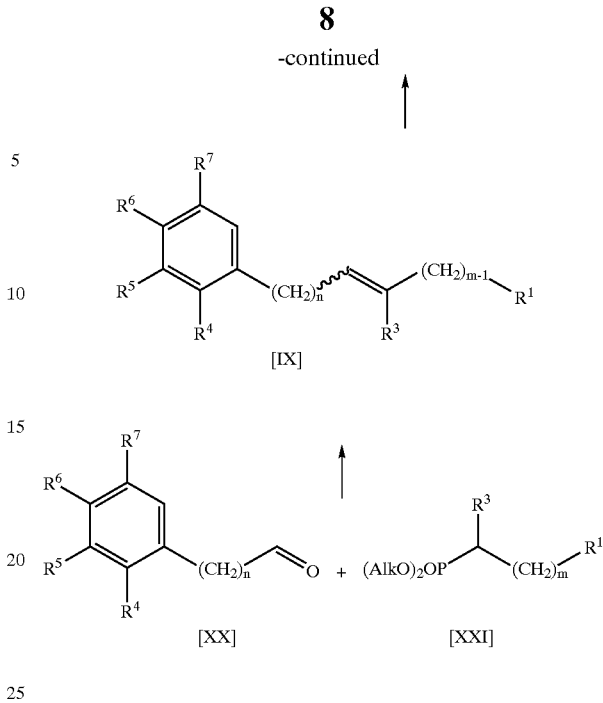

Referring to Scheme 5 and 6, the compounds of formulae [III], [IV], [V], [VI], [XVIII], [XIX], [XX], [XXI] can be prepared by methods well known to those of ordinary skill in the art.

In the above formulae (Scheme 5), X represents a facile leaving group and may be a sulfonate group or a halogen. Preferably, X is selected from chlorine and bromine.

The reactions according to Scheme 5 are usually carried out in the presence of a strong base, as for example metal alkoxides, metal amides, metal hydrides or mixtures thereof. Most preferably, the strong base is selected from sodium methoxide, sodium ethoxide, potassium tert-butoxide, sodium hydride, sodium tert-pentoxide, sodium bis(trimethylsilyl)amide, lithium diisopropylamide or mixtures thereof.

The coupling reaction according to Scheme 6 is usually carried out in the presence of a base. Preferably, the base is selected from metal carbonate, metal alkoxides, metal amides or metal hydrides. More preferably, the base is selected from potassium carbonate, sodium methoxide, sodium ethoxide, potassium tert-butoxide, sodium hydride, lithium diisopropylamide or mixture thereof.

The products of the coupling reaction shown in Scheme 6, i.e compounds [VIII] and [IX] can undergo isomerisation under the reaction conditions to give either an isomeric mixture or the thermodynamically more stable isomer.

The above process can be carried out either without a solvent or in the presence of an organic solvent or water. The organic solvent is preferably selected from tetrahydrofuran (THF), 1,2-dimethoxyethane, dichloromethane, benzene, toluene, N,N-dimethylformamide (DMF), N,N-dimethylacetamide, 1-methyl-2-pyrrolidinone, dimethylsulphoxide (DMSO), methanol, ethanol, isopropanol, tert-butyl alcohol or mixtures thereof.

Scheme 6

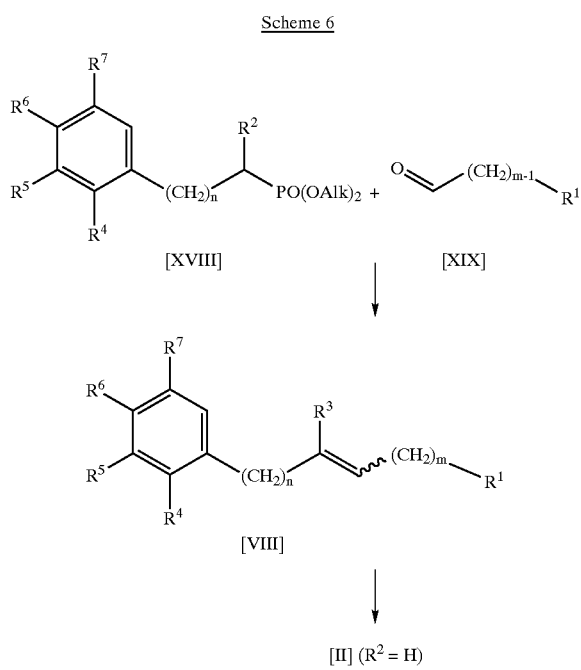

The compounds [VIII] and [IIX] in Scheme 6 can be reduced by catalytic hydrogenation. Transition metals can be used as catalysts in said catalytic hydrogenation. Preferably, Pd, Pt, Rh, Ru or Ni are used. During this process some of the R¹ groups are reduced (e.g. 4-pyridyl—to 4-piperidyl. In such a case it is preferred to protect the nitrogen of the piperidyl group).

A compound of formula [IIa] (Scheme 3) may be prepared from the compounds [IIIa] and [IVa], as shown in the following Schemes 7 and 8.

Scheme 7

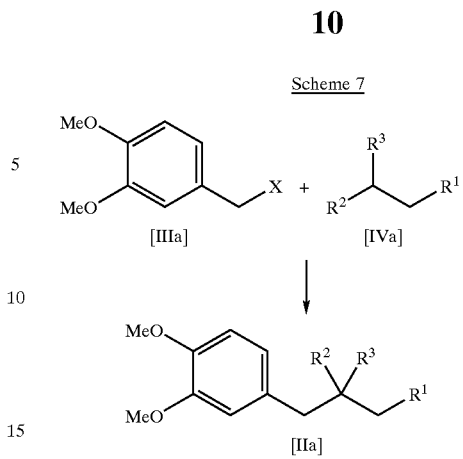

Scheme 8

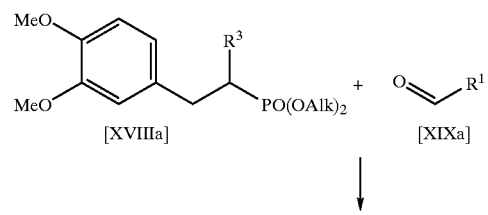

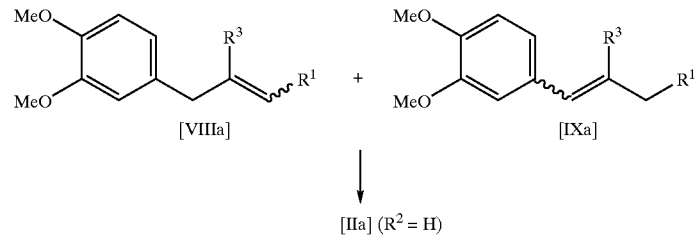

[IIa] (R² = H)

Compounds [XIV] and [XVII] which can be used in the synthesis of Donepezil (Scheme 4) may be prepared according to either Scheme 9 or Scheme 10.

Scheme 9

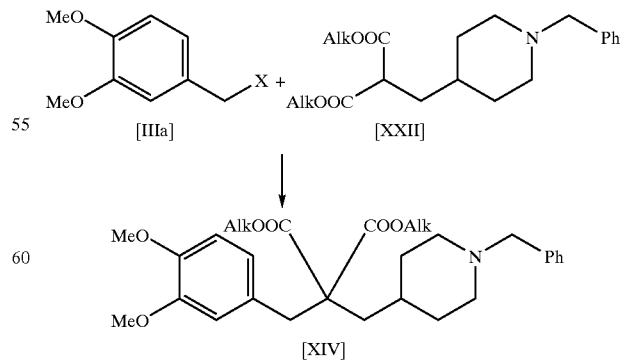

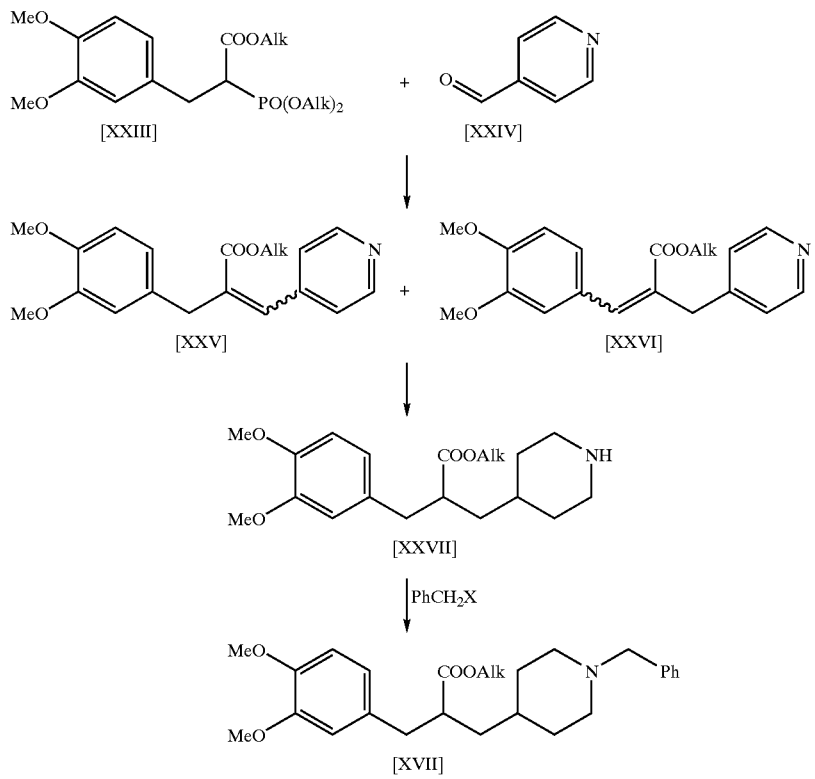

Scheme 10

Enantiomerically enriched compounds of formula [I] are obtained from optically pure compounds [II] (Scheme 2), which in turn, are obtained from a racemic mixture of [II] (wherein $R^2 \neq R^3$) by either of the following reactions:

Diastereomeric crystallisation with optically pure acids, followed by several recrystallisations and recovery of the desired product;

Diastereomeric crystallisation with optically pure amines (if $R^2$ or $R^3$=COOH) followed by a number of recrystallisations and recovery of the desired product;

Resolution on an optically active sorbent;

Enzymatic resolution.

Furthermore, in order to increase the yield of the optically pure product [II], the undesired enantiomer may be racemised and reused.

The present invention will be described in more detail with the aid of the following non-limiting examples.

EXAMPLE 1
Preparation of Donepezil (VII)

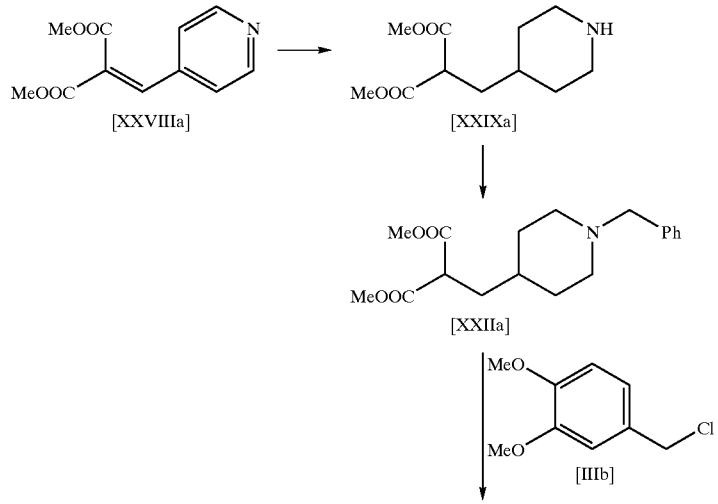

Scheme 11

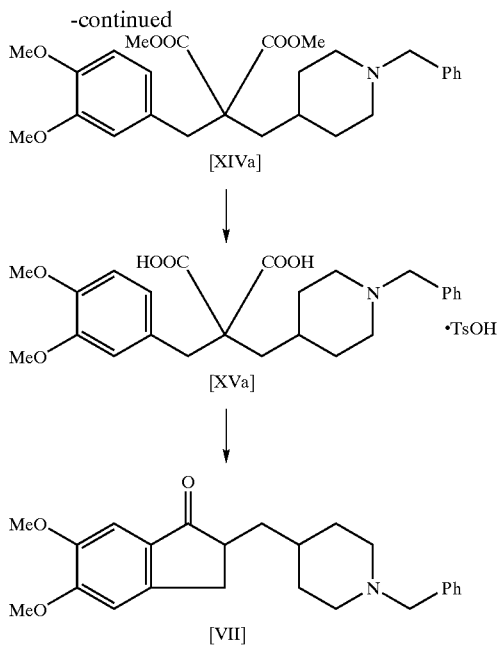

1.1 Preparation of dimethyl (4-piperidylmethyl) malonate [XXIXa]

A solution of dimethyl (4-pyridylmethylene)malonate [XXVIIIa] (925 g) in methanol (9 L) was hydrogenated in the presence of glacial acetic acid (360 mL) and 10% palladium on activated carbon catalyst (92.5 g) at 60° C. and 200 psi. The catalyst was filtered off and the resulting solution of the title compound in the form of acetic acid salt was used directly in the next step.

1.2 Preparation of dimethyl (N-benzyl-4-piperidylmethyl)malonate [XXIIa]

Sodium carbonate (1,550 g) and benzyl chloride (582.3 g) were added to the solution of the acetic acid salt of dimethyl (4-piperidylmethyl)malonate [XXIXa] from the previous step. The obtained slurry was stirred for 12 hours at 60–65° C. and evaporated under reduced pressure. Water was added to the residue and the mixture was extracted with dichloromethane. The organic layer was washed with water, dried over sodium sulfate, passed through short silica gel column and evaporated under reduced pressure. The residue was washed with hexane and dried under reduced pressure to give dimethyl (N-benzyl-4-piperidylmethyl)malonate [XXIIa]. $^1$H NMR (CDCl$_3$) δ1.10–1.37 (m, 3H), 1.50–1.75 (m, 2H), 1.75–2.00 (m, 4H), 2.83 (br. d, 2H, J=12 Hz), 3.44 (s, 2H), 3.70 (s, 6H), 7.26 (m, 5H).

1.3 Preparation of dimethyl (3,4-dimethoxybenzyl)(N-benzyl-4-piperidylmethyl)malonate [XIVa]

A solution of dimethyl (N-benzyl-4-piperidylmethyl) malonate [XXIIa] (43.5 g) in THF (100 mL) obtained in the previous step, was added dropwise to a mixture of sodium hydride, 60% suspension in mineral oil (7.0 g) and THF (60 mL). After the evolution of hydrogen stopped, a solution of 3,4-dimethoxybenzyl chloride [IIIb] (30.7 g) in THF (100 mL) was added dropwise to the mixture. The resulting mixture was refluxed for 3 hours and then cooled to room temperature. A solution of absolute ethanol (5 mL) in 20 mL THF was carefully added to the mixture until the evolution of hydrogen has stopped. Then the reaction mixture was concentrated under reduced pressure to about half volume and treated with a mixture of ice and 5% aqueous citric acid followed by the neutralisation with 5% aqueous sodium hydrogen carbonate solution. The product was extracted with dichloromethane, the organic layer was washed with water, dried over sodium sulfate, passed through a short silica gel column and evaporated to dryness to obtain dimethyl (3,4-dimethoxybenzyl)(N-benzyl-4-piperidylmethyl)malonate [XIVa], $^1$H NMR (CDCl$_3$) δ1.12–1.39 (m, 2H), 1.39–1.60 (m, 3H), 1.77 (d, 2H, J=4 Hz), 1.82–2.02 (m, 2H), 2.80 (br. d, 2H, J=11.3 Hz), 3.18 (s, 2H), 3.43 (s, 2H), 3.63 (s, 6H), 3.77 (s, 3H), 3.79 (s, 3H), 6.51–6.63 (m, 2H), 6.66–6.78 (m, 1H), 7.15–7.33 (m, 5H).

(3,4-Dimethoxybenzyl)(N-benzyl-4-piperidylmethyl) malonate hydrochloride [XIVc] was obtained from [XIVa] by the standard procedure. $^1$H NMR (CDCl$_3$) δ1.43–2.22 (m, 7H), 2.42–2.70 (m, 2H), 3.13 (s, 2H), 3.28–3.50 (m, 2H), 3.67 (s, 6H), 3.79 (s, 3H), 3.82 (s, 3H), 4.07 (br. s, 2H), 6.45–6.65 (m, 2H), 6.70–6.80 (m, 1H), 7.37–7.52 (m, 3H), 7.52–7.73 (m, 2H), 12.32 (m, 1H)

1.4 Preparation of (3,4-dimethoxybenzyl)(N-benzyl-4-piperidylmethyl)malonic acid p-toluenesulfonate [XVa]

A mixture of dimethyl (3,4-dimethoxybenzyl) (N-benzyl-4-piperidyl methyl)malonate [XIVa] (36.0 g), 85% potassium hydroxide (25.3 g), methanol (40 mL) and water (30 mL) was refluxed under stirring for 20 hours. The mixture was evaporated under vacuum and water solution of residue was added dropwise to, the stirred at 0–5° C. solution of p-toluenesulfonic acid monohydrate (100.0 g) in 100 mL of water. The precipitated solid was filtered off, washed with cold water and dried to give (3,4-dimethoxybenzyl)(N-benzyl-4-piperidylmethyl)malonic acid p-toluenesulfonate [XVa].

1.5 Preparation of donepezil [VII]

Phosphorous pentoxide (1.0 g) was dissolved in methanesulfonic acid (10.0 g) at 90° C. (3,4-Dimethoxybenzyl)(N- benzyl-4-piperidylmethyl)malonic acid p-toluenesulfonate [XVa] (2.0 g) were added to the solution at 55° C. The mixture was stirred vigorously for 2 hours at 55–65° C. and poured on crushed ice. The obtained mixture was extracted with dichloromethane. The organic layer was washed with 5% aqueous sodium carbonate solution, dried over anhydrous sodium sulfate, filtered and concentrated under reduced pressure. The crude donepezil was purified by column chromatography on silica gel (dichloromethane methanol from 100:0 to 96:4 v/v) to give donepezil [VII]. $^1$H NMR is in agreement with the literature.

EXAMPLE 2
Preparation of Donepezil [VII]

Scheme 12

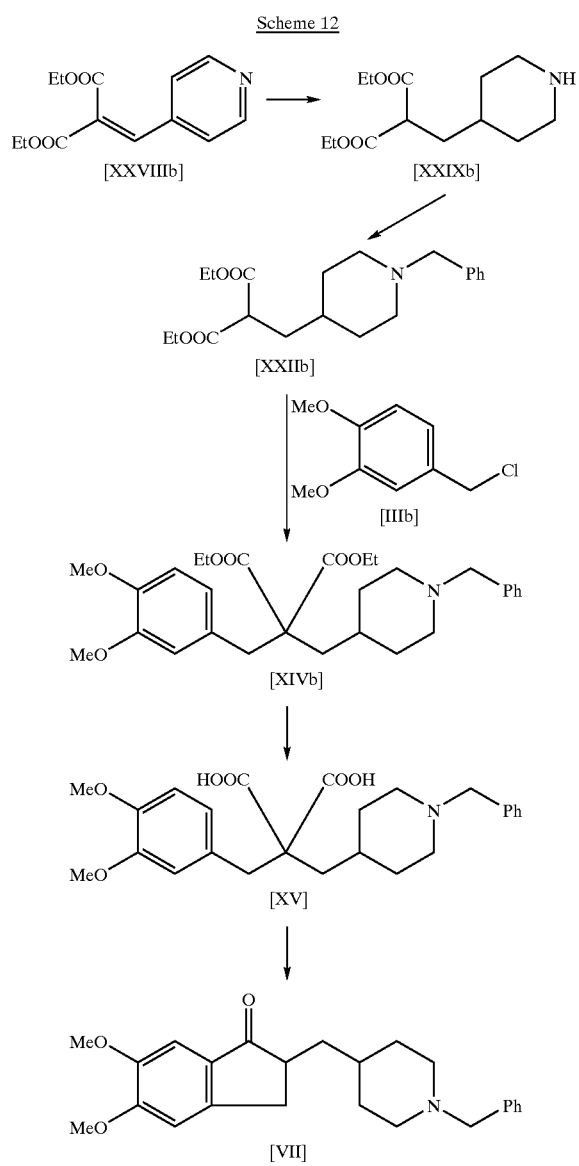

2.1 Preparation of diethyl (4-piperidylmethylene)malonate [XXIXb]

A solution of diethyl (4-pyridylmethylene)malonate [XXVIIIb] (97.6 g) in absolute ethanol (1 L) was hydrogenated in the presence of acetic acid glacial (35.5 g) and 10% Palladium on activated carbon catalyst (9.7 g) at 60° C. and 200 psi for 20 hours. The catalyst was filtered off and the resulting solution of the title compound in the form of acetic acid salt was used directly in the next step.

2.2 Preparation of diethyl (N-benzyl-4-piperidylmethyl)malonate [XXIIb]

Benzyl chloride (54.4 g) and sodium carbonate (149.4 g) were added to the solution of the acetic acid salt of diethyl (4-piperidylmethyl)malonate [XXIXb] from the previous step. The obtained slurry was stirred for 12 hours at 60–65° C. and evaporated under reduced pressure. Water was added to the residue and the obtained mixture was extracted with dichloromethane. The organic layer was washed with water, dried over sodium sulfate, passed through short silica gel column and evaporated under reduced pressure. The obtained residue was washed with hexanes and dried under reduced pressure to give diethyl (N-benzyl-4-piperidylmethyl)malonate [XXIIb].

Diethyl (N-benzyl-4-piperidylmethyl)malonate hydrochloride [XXIIc] was obtained from diethyl (N-benzyl-4-piperidylmethyl)malonate [XXIIb] by the standard procedure. $^1$H NMR (CDCl$_3$), δ1.11 (t, 6H, J=7.1 Hz), 1.25–1.55 (m, 1H), 1.55–2.05 (m, 5H), 2.50–2.77 (m, 2H), 3.23 (t, 1H, J=7.8 Hz), 3.33 (br. d, 2H, J=12.5 Hz), 4.03 (q, 4H, J=7.1 Hz), 4.12 (d, 2H, J=4.8 Hz), 7.28 (m, 3H), 7.53 (m, 2H), 11.67 (m, 1H).

2.3 Preparation of diethyl (3,4-dimethoxybenzyl)(N-benzyl-4-piperidylmethyl)malonate [XIVb]

A solution of diethyl (N-benzyl-4-piperidylmethyl)malonate[XXIIb] (11.3 g) in THF (30 mL) was added dropwise to a mixture of sodium hydride, 60% suspension in mineral oil (1.95 g) and THF (15 mL). After the evolution of hydrogen stopped, 3,4-dimethoxybenzyl chloride [IIIb] (7.3 g) was added to the mixture and the resulting mixture was stirred at 20–25° C. for 12 hours. A solution of absolute ethanol (1 mL) in THF (10 mL) was carefully added under stirring to the cold mixture until the evolution of hydrogen has stopped. Then the reaction mixture was concentrated under reduced pressure to about half volume and treated with a mixture of ice and 5% aqueous citric acid followed by neutralization with aqueous sodium hydrogen carbonate solution. The product was extracted with dichloromethane, the organic layer was washed with water, dried over sodium sulfate, passed through short silica gel column to obtain diethyl (3,4-dimethoxybenzyl)(N-benzyl-4-piperidylmethyl)malonate [XIVb], $^1$H NMR (CDCl$_3$), δ1.19 (t, 6H, J=7.1 Hz), 1.19–1.38 (m, 2H), 1.38–1.63 (m, 3H), 1.77 (d, 2H, J=4.7 Hz), 1.82=2.02 (m, 2H), 2.80 (br. d, 2H, J=11.4 Hz), 3.19 (s, 2H), 3.43 (s, 2H), 3.78 (s, 3H), 3.80 (s, 3H), 4.11 (q, 4H J=7.1 Hz), 6.52–6.65 (m, 2H), 6.65–6.77 (m, 1H), 7.18–7.32 (m, 5H).

Diethyl (3,4-dimethoxybenzyl)(N-benzyl-4-piperidylmethyl)malonate hydrochloride [XIVd] was prepared from diethyl (3,4-dimethoxybenzyl)(N-benzyl-4-piperidylmethyl)malonate [XIVb] according to the standard procedure. $^1$H NMR (CDCl$_3$), δ1.16 (t, 6H, J=7.1 Hz), 1.50–1.85 (m, 5H), 1.85–2.13 (m, 2H), 2.35–2.70 (m, 3H), 3.10 (s, 2H), 3.25–3.45 (m, 2H), 3.74 (s, 3H), 3.77 (s, 3H), 3.97–4.20 (m, 6H), 6.44–6.60 (m, 2H), 6.67 (d, 1H, J=7.9 Hz), 7.28–7.42 (m, 3H), 7.50–7.64 (m, 2H), 12.13 (m,1H)

2.4 Preparation of (3,4-dimethoxybenzyl)(N-benzyl-4-piperidyl-methyl)malonic acid [XV]

A mixture of diethyl (3,4-dimethoxybenzyl)(-benzyl-4-piperidylmethyl)malonate [XIVb] (36.0 g), 85% potassium hydroxide (23.9 g), 96% ethanol (40 mL) and water (30 mL) was refluxed for 20 hours. After evaporation of ethanol, the residual aqueous solution was acidified with 32% hydrochloric acid to pH 4 at 0–5° C. The precipitated solid was filtered off, washed with water and dried to give (3,4-dimethoxybenzyl)(N-benzyl-4-piperidylmethyl)malonic acid [XV], NMR $^1$H (DMSO-d$_6$) δ0.81–1.09 (m, 2H), 1.25 (br. s, 2H), 1.25–1.48 (m, 3H), 1.74–1.93 (br. t, 2H), 2.60 (br. d, 2H, J=10.7 Hz), 2.89 (s, 2H), 3.28 (s, 2H), 3.59 (s, 6H), 6.56 (br. d, 1H, J=8.0 Hz), 6.64 (br. s, 1H), 6.69 (d, 1H, J=8.0 Hz), 7.15 (m, 5H); NMR $^1$H (NaOD-D$_2$O) δ1.10–1.95 (m, 7H), 2.42–3.68 (m, 8H), 3.68 (s, 6H), 4.18 (s, 2H), 6.60–6.90 (m, 4H), 7.43 (m, 3H), 7.59 (m, 2H), 10.78 (m, 1H).

2.5 Preparation of donepezil [VII]

Phosphorous pentoxide (1.0 g) was added to methanesulfonic acid (10.0 g, 104 mmol) and the mixture was stirred at 90° C. to complete dissolution of phosphorous pentoxide. The mixture was cooled to 55° C. and (3,4-dimethoxybenzyl)(N-benzyl4-piperidylmethyl)malonic acid [XV] (2.0 g) was added over a period of 10 min. The obtained mixture was stirred vigorously for 2 hours at 55–65° C. The reaction mixture was poured into crushed ice and extracted with dichloromethane. The organic layer was washed with aqueous sodium carbonate, dried over sodium sulfate, filtered and concentrated under reduced pressure. The crude donepezil was purified by column chromatography on silica gel (dichloromethane:methanol from 100:0 to 96:4) to give donepezil [VII] NMR $^1$H (CDCl$_3$) is in agreement with the literature.

EXAMPLE 3

Preparation of Donepezil

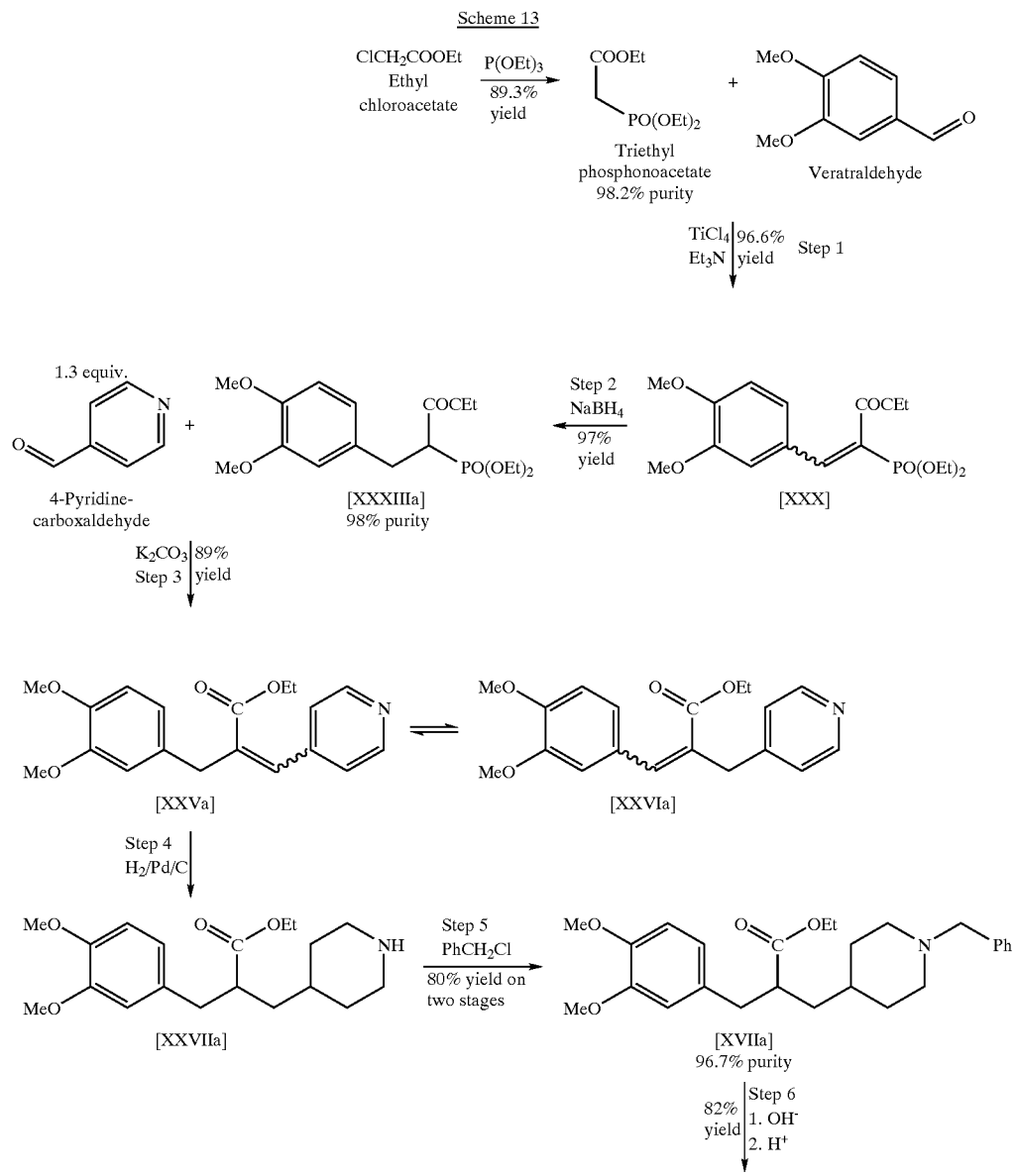

Scheme 13

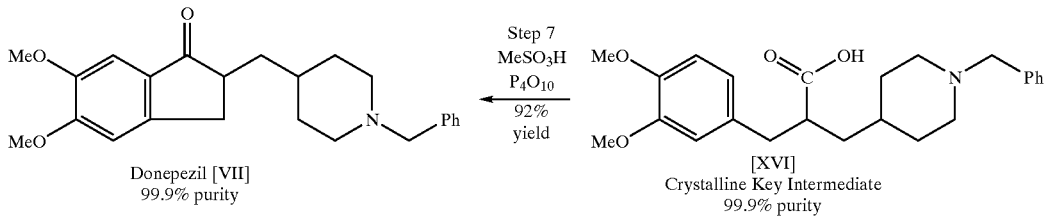

Donepezil [VII]
99.9% purity

[XVI]
Crystalline Key Intermediate
99.9% purity

Total yield of donepezil from veratraldehyde through steps 1–7 was 50.3% and 41.3% from 4-pyridinecarboxaldehyde through steps 3–7

3.0 Preparation of triethyl phosphonoacetate

A 10 L glass reactor equipped with a mechanical stirrer, a digital thermometer, a heating mantle and a reflux condenser, connected to a distillation head was charged with triethyl phosphite (3.69 Kg, 22.2 mol) and ethyl chloroacetate (2.72 Kg, 22.2 mol). The reactor was filled with argon and the reaction mixture was heated to 120° C. The stirring was continued for 3 hours and the temperature of the solution was raises to 165° C., during this time some triethyl phosphite and ethyl chloroacetate was distilled off. Then, the reaction mixture was heated to 174° C. and the solution was left overnight. The reaction mixture was fractionationally distilled under reduced pressure (10–11 mbar) to give 4.43 Kg (89.3% yield) triethyl phosphoacetate with 98.2% purity by GC.

3.1 Preparation of triethyl 3,4-dimethoxy-α-phosphonocinnamate [XXX]

A 100 L glass reactor equipped with a mechanical stirrer, a dropping funnel, a thermometer and a bubbler was charged with veratraldehyde (3.45 Kg, 20.8 mol), triethyl phosphonoacetate (4.65 Kg, 20.7 mol) and dichloromethane (53.5 Kg) and filled with argon. The solution of titanium (IV) chloride (7.87 Kg, 41.5 mol) in dichloromethane (16.2 Kg) was added dropwise to the stirred mixture while keeping the temperature between −5° and 0° C. The mixture was stirred for an additional 2 hours at the same temperature. Triethylamine (8.40 Kg, 83.0 mol) was added dropwise to the stirred mixture for three hours while keeping the temperature between −5 and 0° C. The obtained mixture was stirred for an additional 0.5 hour at the same temperature. The reaction mixture was poured under stirring into water at 20÷25° C. The organic layer was separated and aqueous layer was extracted with dichloromethane. The combined organic extracts were consequently washed with water, sodium hydrogencarbonate aqueous solution and again with water. The organic layer was dried over sodium sulfate, passed through silica gel column and the solvent was removed under reduced pressure to afford 7.45 Kg (96.6% yield) of triethyl 3,4-dimethoxy-α-phosphonocinnamate [XXX] as yellow oil.

$^1$H NMR (CDCl$_3$) δ1.20–1.39 (m, 9H), 3.79 (s, 3H), 3.84 (s, 3H), 4.11 (p, 4H, J=7.4 Hz), 4.24 (q, 2H, J=7.2 Hz), 6.80 (d, 1H, J=8.3 Hz), 6.97 (d, 1H), 7.00 (dd, 1H, J=8.3 Hz), 7.49 (d, 1H, J=24.4 Hz).

This material was used in the next stage without further purification.

3.2 Preparation of triethyl (3,4dimethoxybenzyl) phosphonoacetate [XIIIa]

A 100 L glass reactor equipped with a mechanical stirrer, a thermometer, a dropping funnel and a bubbler was charged with triethyl 3,4-dimethoxy-α-phosphonocinnamate [XXX] (6.86 Kg, 18.4 mol) and abs. ethanol (26.0 Kg) and filled with argon. A solution of sodium borohydride (261.0 g, 6.90 mol) in abs. ethanol (7.0 Kg) was added dropwise to the mixture under stirring for 3 hours while keeping the temperature of the mixture at 0–5° C. The obtained mixture was stirred for 3.5 h at 15–20° C. Glacial acetic acid (770.0 g, 12.8 mol) was added dropwise to the mixture at 15–20° C. The reaction mixture was stirred 0.5 h at the same temperature and the solvent was removed under reduced pressure. The residue was dissolved in a mixture of dichloromethane (15 Kg) and water (13 Kg). An organic layer was separated and the aqueous layer was extracted with dichloromethane. The combined organic layers were washed with water, dried over sodium sulfate, passed through a short silica gel column and solvent was removed under reduced pressure to afford 6.72 Kg (97% yield) of triethyl (3,4-dimethoxybenzyl) phosphonoacetate [XXIIIa] 98% purity by GC as yellow oil which was not further purified.

$^1$NMR (CDCl$_3$) d 1.04 (t, 3H, J=7.2 Hz), 1.19–1.27 (m, 6H), 3.04–3.22 (m, 3H), 3.71 (s, 3H), 3.73 (s, 3H), 3.90–4.10 (m, 6H), 6.55–6.70 (m, 3H).

3.3 Preparation of isomeric mixture of ethyl 2-(3,4-dimethoxy-benzyl)-3-(4-pyridyl)acrylate [XXVa] and ethyl 3,4-dimethoxy-α-(4-pyridylmethyl) cinnamate [XXVIa]

A 100 L glass reactor equipped with a mechanical stirrer, a thermometer, a dropping funnel and a bubbler was charged with triethyl (3,4-dimethoxybenzyl)phosphonoacetate [XXIIIa] (13.44 Kg, 35.4 mol) is and 4-pyridinecarboxaldehyde (5.00 Kg, 46.7 mol) and filled with argon. A solution of potassium carbonate (15.10 Kg, 109 mol) in water (15.1 Kg) was added dropwise to the mixture under stirring while keeping the temperature of the mixture at 10–15° C. The obtained mixture was stirred overnight at 15–20° C. and kept without stirring for 3 hours at the same temperature. Upper organic layer was separated and water was added to the aqueous layer. The obtained aqueous solution was extracted with dichloromethane. The combined organic layers were washed with water, dried over sodium sulfate, passed through a short silica gel column and the solvent was removed under reduced pressure to afford 10.47 Kg (89% yield) of a mixture of [XXVa] and [XXVIa] as yellow oil. The mixture was used in the next stage without further purification.

Analytical samples of [XXVa] and [XXVIa] were separated from the mixture by column chromatography on silica gel (hexanes-ethyl acetate from 100:0 to 0:100 v/v).

[XXVa]: $^1$H NMR (CDCl$_3$) δ1.22 (t, 3H, J=7.1 Hz), 3.75–3.85 (m, 8H), 4.18 (q, 2H, J=7.1 Hz), 6.55–6.65 (m. 2H), 6.74 (d, 1H, J=8.8 Hz), 7.21 (d, 2H, J=5.7 Hz), 7.71 (s, 1H), 8.56 (d, 2H, J=5.7 Hz)

[XXVIa]: $^1$H NMR (CDCl$_{13}$) δ1.01 (t, 3H, J=7.1 Hz), 3.68 (s, 2H), 3.83 (s, 6H), 4.04 (q, 2H, J=7.1 Hz), 6.44 (s, 1H), 6.70–6.80 (m, 3H), 7.12 (d, 2H, J=5.8 Hz), 8.50 (d, 2H, J=5.9 Hz)

3.4 Preparation of ethyl 2-(3,4-dimethoxybenzyl)-3-(4-piperidine)propionate [XXVIIa]

A 18 L stainless steel high pressure "Parr" reactor was charged with 10 wt. % palladium on activated carbon (175 g), sodium acetate (262 g), glacial acetic acid (480 g), a mixture of [XXVa] and [XXVIa] (1200 g, 3.67 mol), abs. ethanol (12 L) and filled consequently with nitrogen and hydrogen. The hydrogenation was carried out at hydrogen pressure of 250 psi at 90° C. Then, the reactor was cooled to room temperature and the catalyst was filtered off (the catalyst may be used repeatedly in following reactions). The obtained solution of [XXVIIa] was used for the next step without further purification.

[XXVIIa]: $^1$H NMR (CDCl$_3$) δ1.09 (t, 3H, J=7.1 Hz), 0.80–1.45 (m, 4H), 1.45–1.80 (m, 3H), 2.35–2.90 (m, 5H), 2.97 (br. d, 2H, J=12.2 Hz), 3.79 (s, 6H), 3.90–4.05 (m, 2H), 6.55–6.65 (m, 2H), 6.71 (d, 1H, J=8.7 Hz)

Ethyl 2-(3,4-dimethoxybenzyl)-3-(4-piperidine)propionate hydrochloride [XXVIIb] was prepared from [XXVIIa] by the standard procedure.

[XXVIIb]: $^1$H NMR (CDCl$_3$) δ1.13 (t, 3H, J=7.2 Hz), 1.30–2.00 (m, 7H), 2.55–2.90 (m, 5H), 3.41 (br. d, 2H, J=12.5 Hz), 3.83 (s, 6H1), 4.04 (q, 2H, J=7.2 Hz), 6.55–6.70 (m, 2H), 6.74 (d, 1H, J=8.3 Hz), 9.05–9.25 (m, 1H), 9.40–9.60 (m, 1H).

3.5 Preparation of ethyl 2-(3,4-dimethoxybenzyl)-3-(N-benzyl-4-piperidine)propionate [XVIIa].

A 20 L glass reactor, equipped with a heating mantle, a mechanical stirrer, a thermometer, a dropping funnel and a condenser connected to a bubbler was charged with the solution of [XXVIIa] from the previous step, sodium carbonate (1.35 Kg, 12.7 mol) and benzyl chloride (743.0 g, 5.87 mol) and filled with argon. The mixture was stirred at 60–65° C. for 8 h and evaporated under reduced pressure. Water (6.0 Kg) and toluene (3.8 Kg) were added to the residue. The mixture was stirred at room temperature until complete disappearance of solid phase. The organic layer was separated and the aqueous layer was extracted with toluene. The combined organic solution was extracted with 20% aqueous solution of citric acid (7.8 Kg). The aqueous solution was basified to pH 10 with sodium carbonate and extracted with dichloromethane. The organic extract was dried over sodium sulfate, filtered, passed through short silica gel column and evaporated under reduced pressure to give 1.82 Kg (80% yield from the mixture of compounds [XXVa] and [XXVIa]) of the compound [XVIIa] as yellow oil with 96.7% purity by GC.

$^1$H NMR (CDCl$_3$) δ1.08 (t, 3H, 7.1 Hz), 1.10–1.90 (m, 7H), 2.10–2.35 (m, 2H), 2,55–3.00 (m, 3H), 3.15 (br. d, 2H, J=10.4 Hz), 3.80 (s, 8H), 3.98 (q, 2H, J=7.1 Hz), 6.55–6.65 (m, 2H), 6.72 (d, 1H, J=8.6 Hz), 7.31 (s, 5H).

The product was used in the next stage without further purification.

3.6 Preparation of 2-(3,4-dimethoxybenzyl)-3-(N-benzyl-4-piperidine)propionic acid [XVI]

A 100 L glass reactor equipped with a mechanical stirrer, a thermometer and a condenser connected to a bubbler was charged with ethyl 2-(3,4-dimethoxybenzyl)-3-(N-benzyl-4-piperidine)propionate [XVIIa] (4.50 Kg, 10.6 mol), 90% potassium hydroxide (1.02 Kg, 16.4 mol), methanol (5.0 Kg) and water (5.0 Kg) and filled with argon. The mixture was refluxed under stirring for 3.5 hours, cooled to room temperature and washed with toluene (2×4.0 Kg). An aqueous layer was acidified to pH 8 with 20% aqueous solution of citric acid and water (10.0 Kg) was added to the mixture. Methanol (4.0 Kg) was evaporated from the suspension at 90° C. The obtained mixture was stirred at 0° C. for about 3 hours. The precipitated crystalls were filtered off and washed on filter with water. The wet crude product was dissolved in methanol (8.0 Kg). Water (22.0 Kg) was added to the vigorously stirred solution and methanol (4.0 Kg) was evaporated at 90° C. The mixture was stirred for 3 hours at 0–5° C. The precipitated crystalls were filtered off, washed on filter with water and dried at 60° C. under reduced pressure. The crystalline residue was triturated with acetone (10 Kg), filtered off, washed on filter with cold acetone and dried under reduced pressure at 60° C. to give 3.28 Kg (82% yield) of 2-(3,4-dimethoxybenzyl)-3-(N-benzyl-4-piperidine)propionic acid [XVI] as off-white crystals with 99.9% purity by HPLC, mp 116–118° C. Assay by non-aqueous titration 98.7% (on dry basis), water content (KF)—0.96%.

$^1$H NMR (DMSO-D$_6$) δ0.90–1.42 (m, 4H), 1.42–2.07 (m, 5H), 2.46–2.92 (m, 5H), 3.40 (s, 2H), 3.69 (s, 3H), 3.70 (s, 3H), 6.66 (br. d, 1H, J=8.2 Hz), 6.75 (br s, 1H), 6.81 (d, 1H, J=8.2 Hz), 7.18–7.42 (m, 5H).

3.7 Preparation of donepezil [VII]

A 50 L glass reactor equipped with a mechanical stirrer, a dropping funnel, a thermometer and a condenser connected to a bubbler was charged with phosphorus pentoxide (1.40 Kg) and methanesulfonic acid (13.37 Kg) and filled with argon. The mixture was stirred at 70–80° C. until complete homogenization. Dichloromethane (4.0 Kg) and 2-(3,4-dimethoxybenzyl)-3-(N-benzyl-4-piperidine)propionic acid [XVI] (2.50 Kg, 6.29 mol) were added to the mixture at 35–40° C. The obtained mixture was stirred under reflux for 1.5 hour. A 100 L glass reactor equipped with a mechanical stirrer was charged with crushed Ice (18.0 kg) and filled with argon. The cold reaction mixture was added to the ice and the mixture was stirred for 15 min. The aqueous layer of the mixture was adjust to pH 8.0 by addition potassium hydroxide to the stirred mixture at 10–15° C. The organic layer was separated and the aqueous layer was extracted with dichloromethane. The combined organic extracts were dried over sodium sulfate, passed through short silica gel column and evaporated under reduced pressure. The residue* (2.40 Kg, quantitative yield, one spot on TLC) was dissolved in diisopropyl ether. The obtained solution was kept overnight at room temperature and 2 hours at 0–5° C. The precipitated crystals were filtered off, washed with diisopropyl ether and dried under reduced pressure to give 2.21 Kg (92% yield) of donepezil [VII] as off-white crystals with 99.9% purity by HPLC. $^1$H NMR (CDCl$_3$) is in agreement with the literature.

* A small portion of the residue was dissolved in methylene chloride. A 10% solution of hydrogen chloride in ethyl acetate was added to the resulting solution, followed by concentration under reduced pressure to obtain a crystals, which was twice recrystallized from methanol-isopropyl ether to obtain with 85% yield donepezil hydrochloride, 100.0% purity by HPLC, mp 220–221° C.

EXAMPLE 4

Preparation of 5,6-dimethoxy-2-(N-benzoyl-4-piperidylmethyl)-1-oxoindane [XXXIV]

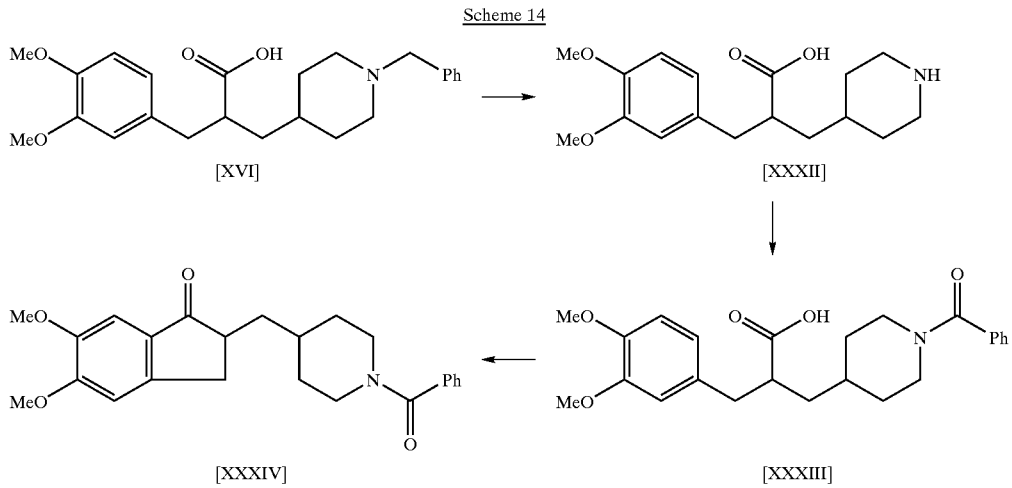

Scheme 14

4.1 Preparation of 2-(3,4-dimethoxybenzyl)-3-(4-piperidine)propionic acid [XXXII]

A 2 L stainless steel high pressure "Parr" reactor was charged with 10 wt. % palladium on activated carbon (4.0 g), glacial acetic acid (20.8 g), 2-(3 4-dimethoxybenzyl)-3-(N-benzyl-4-piperidine)propionic acid [XVI] (86.0 g) and methanol (1.0 L) and filled consequently with nitrogen and hydrogen. The hydrogenation was carried out at hydrogen pressure from 100 to 150 psi at 60° C. for 2.5 h. The reactor was cooled to room temperature and catalyst was filtered off. The obtained solution was evaporated under reduced pressure to give 2-(3,4-dimethoxybenzyl)-3-(4-piperidine)propionic acid [XXXII].

1H NMR (D$_2$O) δ0.90–1.50 (m, 5H), 1.50–1.75 (m, 2H), 2.30–2.55 (m, 3H), 2.55–2.78 (m, 2H), 3.02–3.18 (m, 2H), 3.51 (s, 3H), 3.55 (s, 3H), 6.50 (br.d, 1H, J=7.8 Hz), 6.55–6.63 (m, 2H)

4.2 Preparation of 2-(3,4-dimethoxybenzyl)-3-(N-benzoyl-4-piperidine)propionic acid [XXXIII]

A 2 L glass round bottom flask equipped with an ice-water bath, a magnetic stirrer, a thermometer, a dropping funnel and a bubbler was charged with 2-(3,4-dimethoxybenzyl)-3-(4-piperidine)propionic acid [XXXII] (50 g), potassium carbonate (138.0 g), water (0.75 L) and filled with argon. Benzoyl chloride (42.9 g) was added dropwise to the stirred mixture at 5–10° C. The obtained mixture was stirred for 3 h at room temperature. A 16 wt. % hydrochloric acid was added dropwise to the mixture at 10–15° C. until reaching pH 3. The mixture was stirred for 1 h at the same temperature. The precipitated solid was filtered off, washed with water and dried under reduced pressure to give the desired 2-(3,4-dimethoxybenzyl)-3-(N-benzoyl-4-piperidine)propionic acid [XXXIII].

$^1$H NMR (CDCl$_3$) δ0.88–1.95 (m, 7H), 2.55–3.05 (m, 5H), 3.60–3.80 (m, 1H), 3.82 (s, 3H), 3.83 (s, 3H), 4.55–4.78 (m, 1H), 6.65–6.70 (m, 2H), 6.75 (d, 1H, J=8.7 Hz), 7.30–7.50 (m, 5H)

4.3 Preparation of 5,6-dimethoxy-2-(N-benzoyl-4-piperidylmethyl)-1-oxoindane [XXXIV]

A 250 mL round bottom flask equipped with a water bath, a magnetic stirrer and a condenser connected to a bubbler was charged with Phosphorus pentoxide (15.1 g) and methanesulfonic acid (145 g) and filled with argon. The mixture was stirred at 75° C. until a complete disappearance of the solid phase and cooled to 35–40° C. Dichloromethane (50 mL) and 2-(3,4-dimethoxybenzyl)-3-(N-benzoyl-4-piperidine)propionic acid [XXXIII] (27.4 g) were added to the mixture. The obtained mixture was refluxed under stirring for 1.5 hour. The reaction mixture was cooled to room temperature and poured into Ice. The organic layer was separated and water layer was extracted with dichloromethane. The combined organic solution was washed with sodium carbonate aqueous solution, dried over sodium sulfate, passed through a short silica gel column and evaporated to dryness. The crystalline residue (25.1 g, 96.2% yield, lone spot on TLC) was re-crystallized from the mixture of methanol and isopropyl ether to give 21.5 g (82.4% yield) of compound [XXXIV] as off-white crystals.

$^1$H NMR (CDCl$_3$) δ1.07–1.48 (m,3H), 1.58–2.00 (m, 4H), 2.62–3.12 (m, 4H), 3.24 (dd, 1H, J=17.5, 8.1 Hz), 3.65–3.85 (m, 1H), 3.88 (s, 3H), 3.93 (s, 3H), 4.62–4.82 (m, 1H), 6.83 (s, 1H), 7.14 (s, 1H), 7.36 (s, 5H)

EXAMPLE 5

Preparation of 2-(N-benzyl-4-piperidylmethyl)-1-oxoindane hydrochloride [VIIb]

Scheme 15

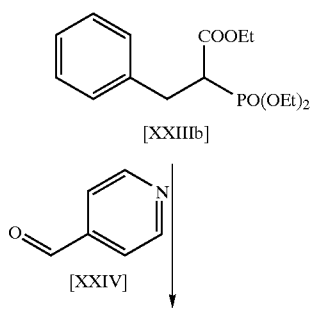

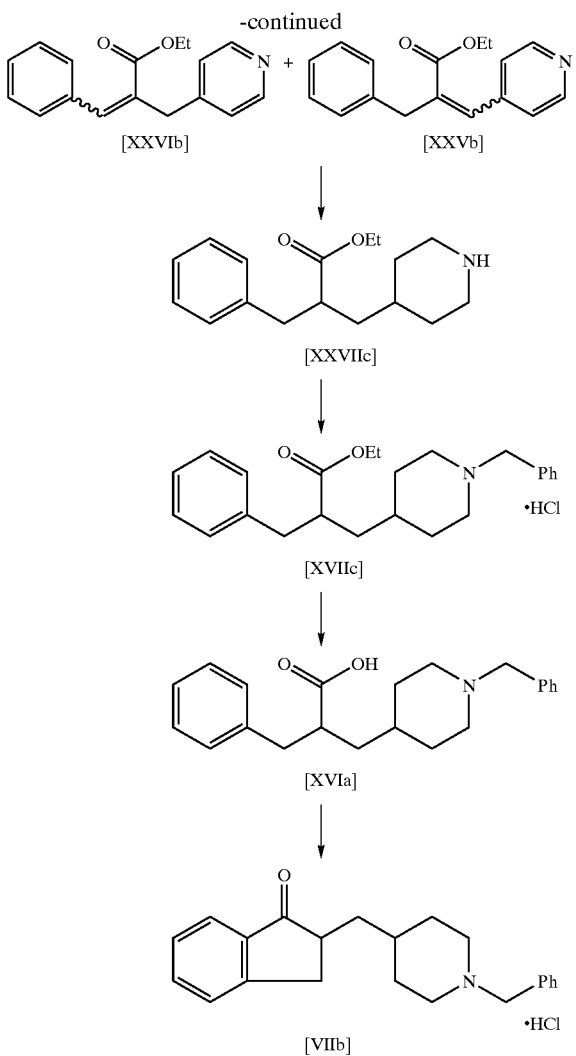

5.1 Preparation of an isomeric mixture of ethyl 2-benzyl-3-(4-pyridyl)acrylate [XXVb] and ethyl α-(4-pyridylmethyl)-cinnamate [XXVIb]

A 250 mL glass round bottom flask equipped with an ice-water bath, a mechanical stirrer, a thermometer, a dropping funnel and a bubbler was charged with triethyl benzylphosphonoacetate [XXIIIb] (82.6 g) and 4-pyridinecarboxaldehyde (39.8 g) and filled with argon. A solution of potassium carbonate (109.5 g) in water (105.0 g) was added dropwise to the mixture at 10–15° C. The obtained mixture was stirred for 22 h at room temperature, diluted with water and extracted twice with dichloromethane. The combined organic layer was dried over sodium sulfate, passed through short silica gel column and evaporated under reduced pressure to give 60.0 g (85.4% yield) of a mixture of [XXVb] and [XXVIb] which was used in the next step without furter purification.

[XXVb]: $^1$H NMR (CDCl$_3$) δ1.20 (t, 3H, J=7.1 Hz), 3.86 (s, 2H), 4.17 (q, 2H, J=7.1 Hz), 7.75 (s, 1H), 8.56 (d, 2H, J=5.6 Hz)

[XXVIb]: $^1$H NMR (CDCl$_3$) δ0.97 (t, 3H, J 7.1 Hz), 3.73 (s, 2H), 4.01 (q, 2H, J=7.1 Hz), 6.47 (s, 1H), 7.08 (d, 2H, J=5.7 Hz), 8.49 (d, 2H, J=5.7 Hz)

5.2 Preparation of ethyl 2-benzyl-3-(4-piperidine) propionate [XXVIIc]

A 2 L stainless steel high pressure "Parr" reactor was charged with 10 wt. % palladium on activated carbon (4.0 g), glacial acetic acid (26.0 g), mixture of [XXVb] and [XXVIb] from previous stage (60.0 g) and abs. ethanol (1.0 L) and filled consequently with nitrogen and hydrogen. The hydrogenation was carried out under hydrogen pressure of 250 psi at 90° C. Then, the reactor was cooled to room temperature and the catalyst was filtered off. The obtained solution of [XXVIIc] was used in the next step without further purification.

5.3 Preparation of ethyl 2-benzyl-3-(N-benzyl-4-piperidine)propionate hydrochloride [XVIIc]

2 L round bottom flask equipped with a heating mantle, a mechanical stirrer, a thermometer, a dropping funnel and a condenser connected to a bubbler was charged with a solution of [XXVIIc] from the previous step, sodium carbonate (73.3 g) and benzyl chloride (32.7 g) and filled with argon. The mixture was stirred at 60–65° C. for 9 h and evaporated under reduced pressure. Water (300 mL) and toluene (300 mL) were added to the residue. The mixture was stirred at room temperature until complete disappearance of solid phase. The organic layer was separated and the aqueous layer was extracted with toluene. The combined organic solution was dried over sodium sulfate, filtered and evaporated under reduced pressure to give 69.5 g (84.7% yield on two stages) of ethyl 2-benzyl-3-(N-benzyl-4-piperidine)propionate [XVIIb] as yellow oil. $^1$H NMR (CDCl$_3$) δ1.10 (t, 3H, J=7.1 Hz), 1.07–1.42 (m, 4H), 1.50–1.78 (m, 3H), 1.78–1.97 (br. t 2H), 2.64–2.97 (m, 5H), 4.02 (q, 2H, J=7.1 Hz), 7.10–7.32 (m, 10 H).

Ethyl 2-benzyl-3-(N-benzyl-4-piperidine)propionate hydrochloride [XVIIc] was obtained from [XVIIb] by the standard procedure. $^1$H NMR (CDCl$_3$) δ1.07 (t, 3H, J=7.1 Hz), 1.27–1.59 (m, 2H), 1.59–2.22 (m, 6H), 2.40–2.98 (m, 5H), 3.38 (br. d, 2H, J=11.6 Hz), 3.99 (q, 2H, J=7.1 Hz), 4.07 (d, 2H, J=4.9 Hz), 7.04–7.71 (m, 10 H), 12.32 (m, 1H).

5.4 Preparation of 2-benzyl-3-(N-benzyl-4-piperidine)propionic acid [XVIIb]

A 500 mL round bottom flask equipped with a heating mantle, a mechanical stirrer, a thermometer and a condenser connected to a bubbler was charged with ethyl 2-benzyl-(N-benzyl-4-piperidine)propionate hydrochloride [XVIIc] (66.9 g), 90% potassium hydroxide (26.0 g), methanol (140 mL) and water (70 mL) and filled with argon. The mixture was refluxed under stirring for 15 h, concentrated under reduced pressure to the volume of about 150 mL, acidified to pH 8 with 20% aqueous solution of citric acid and extracted with dichloromethane. Combined organic extract was dried over sodium sulfate, filtered and evaporated under reduced pressure to give 56.1 g (quantitative yield) of 2-benzyl-3-(N-benzyl-4-piperidine)propionic acid [XVIa].

$^1$H NMR (CD$_3$OD) δ0.80–1.35 (m, 4H), 1.42–1.64 (m. 2H), 1.64–1.97 (m, 3H), 2.38–2.59 (m, 2H), 2.67–2.94 (m, 3H), 3.37 (s, 2H), 6.97–7.26 (m, 10 H).

5.5 Preparation of 2-(N-benzyl-4-piperidylmethyl)-1-oxoindane hydrochloride [VIIb]

A 250 mL round bottom flask equipped with a mechanical stirred, a dropping funnel, a thermometer and a condenser connected to a bubbler was charged with phosphorus pentoxide (13.3 g) and methanesulfonic acid (133 g) and filled with argon. The mixture was stirred at 90–95° C. until complete homogenization. Dichloromethane (40 mL) and 2-benzyl-3-(N-benzyl-4-piperidine)propionic acid [XVIa] (26.6 g) were added to the mixture at 35–40° C. The obtained mixture was stirred under reflux for 3 hours. Then the cold reaction mixture was poured into crushed ice and the mixture was made basic with aqueous potassium hydroxide to pH 9–10. The mixture was extracted with dichloromethane. The combined organic extract was dried over sodium sulfate, passed through short silica gel column and evaporated under reduced pressure. The residue (25.1 g, quantitative yield, one spot on TLC) was treated with a solution of hydrogen chloride in methanol and the resulting solid was recrystallised from mixture of methanol-ether to give 24.3 g (86.5% yield) of compound [VIIb], mp 199–200° C.

$^1$H NMR (CDCl$_3$) δ1.40–2.23 (m, 8H), 2.53–2.83 (m, 4H), 3.23–3.57 (m, 3H), 4.12 (d, 2H, J=4.9 Hz), 7.26–7.72 (m, 9H), 12.26 (m, 1H)

What is claimed is:

1. A process for the preparation of a compound of formula [Ib] including optical isomers and salts

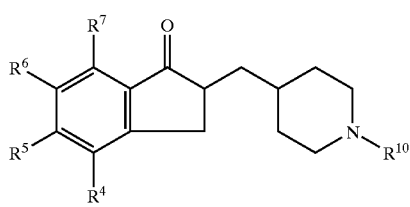

wherein:
$R^4$, $R^5$, $R^6$ and $R^7$ are identical or different and each represents hydrogen, $C_{1-6}$ alkyl, $C_{1-6}$ alkoxy, or halogen;
$R^{10}$ is selected from benzyl, $C_{1-6}$ alkyl, ω-aralkyl, acyl and $C_{1-6}$ alkoxycarbonyl,
which process comprises the following steps:
a) reacting a compound of the following formula

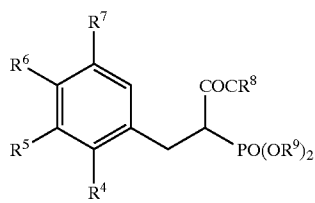

wherein $R^8$ and $R^9$ are identical or different and each represents $C_{1-6}$ alkyl and $R^4$, $R^5$, $R^6$ and $R^7$ are as defined above
with 4-pyridinecarboxaldehyde in the presence of base to give a compound of the formula

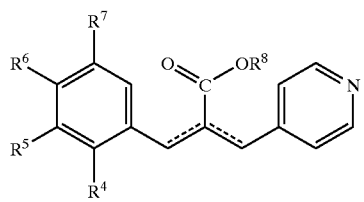

wherein the dotted lines represent two possible locations of the double bond formed in the reaction, $R^4$, $R^5$, $R^6$, $R^7$ and $R^8$ are as defined above, including tautomers, stereoisomers or mixtures thereof as well as acid addition salt thereof;

b) catalytic hydrogenation of the compound or mixture of compounds or their salts obtained in step (a) to give a compound of the following formula

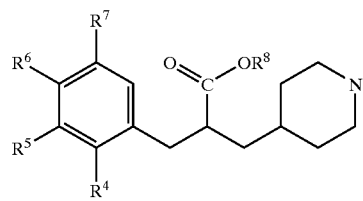

wherein $R^4$, $R^5$, $R^6$, $R^7$ and $R^8$ are as defined above, as well as acid addition salt thereof;

c) reacting the compound obtained in step b) above or a salt thereof with a compound of formula $R^{10}X$, wherein $R^{10}$ is as defined above and X is a leaving group, to yield a compound of the following formula

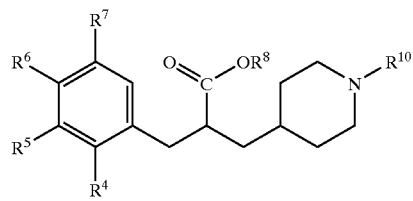

wherein $R^4$, $R^5$, $R^6$, $R^7$, $R^8$ and $R^{10}$ are as defined above, or its salt; following hydrolysis of the ester group to form the corresponding carboxylic acid or a salt thereof;

d) intramolecular cyclization of the carboxylic acid obtained in step c) above or salts thereof to yield the compound [Ib];

e) optionally converting the resulting compound of formula [Ib] into a pharmacologically acceptable salt.

2. Process according to claim 1 wherein $R^4$ and $R^7$ are hydrogen, $R^5$ and $R^6$ are each methoxy.

3. Process according to claim 1, wherein said compound of formula [Ib] is donepezil.

4. A compound of the formula

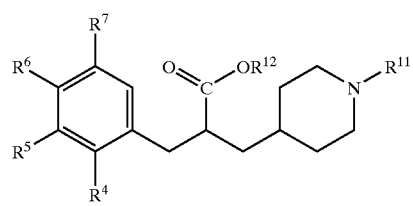

wherein $R^4$, $R^5$, $R^6$ and $R^7$ are as defined in claim 1, $R^{11}$ is hydrogen or is selected from benzyl, $C_{1-6}$ alkyl, ω-aralkyl, acyl and $C_{1-6}$ alkoxycarbonyl, $R^{12}$ is hydrogen or $C_{1-6}$ alkyl, including optical isomers and salts thereof.

5. A compound of the formula

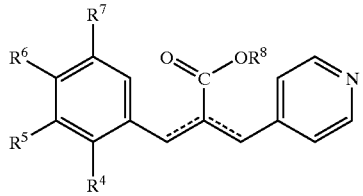

wherein the dotted lines represent two possible locations of the double bond, $R^4$, $R^5$, $R^6$ and $R^7$ are identical or different and each represents hydrogen, $C_{1-6}$ alkyl, or halogen; and $R^8$ is $C_{1-6}$ alkyl, including tautomers, stereoisomers or mixtures thereof as well as acid addition salt thereof, with the proviso that when three of $R^4$–$R^7$ are H, the other one is halogen or $C_{1-6}$ alkoxy.

* * * * *